US007170520B2

(12) United States Patent
Yang

(10) Patent No.: US 7,170,520 B2
(45) Date of Patent: Jan. 30, 2007

(54) DISPLAY FOR SHARING DISPLAY DATA CHANNEL

(75) Inventor: Jung-Yi Yang, Jungli (TW)

(73) Assignee: Delta Electronics, Inc., Taoyuan Hsien (TW)

( * ) Notice: Subject to any disclaimer, the term of this patent is extended or adjusted under 35 U.S.C. 154(b) by 497 days.

(21) Appl. No.: 10/704,026

(22) Filed: Nov. 6, 2003

(65) Prior Publication Data

US 2005/0073511 A1    Apr. 7, 2005

(30) Foreign Application Priority Data

Oct. 3, 2003    (TW) ............................... 92127397 A

(51) Int. Cl.
  *G06T 1/00*    (2006.01)
  *G06T 1/60*    (2006.01)
  *G06T 13/14*   (2006.01)
  *G06T 15/00*   (2006.01)

(52) U.S. Cl. ...................... 345/530; 345/501; 345/519; 345/520

(58) Field of Classification Search ................ 345/3.1, 345/112, 204, 522, 698, 12, 82, 501–574; 349/110; 710/20, 21
See application file for complete search history.

(56) References Cited

U.S. PATENT DOCUMENTS

| 5,691,741 A | * | 11/1997 | Kerigan et al. ............. 345/698 |
| 6,873,307 B2 | * | 3/2005 | Nitta et al. ................... 345/3.1 |
| 2003/0025685 A1 | * | 2/2003 | Shirasaki et al. ........... 345/204 |
| 2004/0027515 A1 | * | 2/2004 | Itakura ........................ 349/110 |

* cited by examiner

*Primary Examiner*—Bipin Shalwala
*Assistant Examiner*—David L. Lewis
(74) *Attorney, Agent, or Firm*—J.C. Patents

(57) ABSTRACT

A display for sharing the display data channel is provided. The display shares the display data channel and thus the preexisting display data channel can be used as the interface for RS232 or I²C communication for performing the ISP or adjustment of the firmware. Hence, it can simplify the manufacturing tools, enhance the manufacturing efficiency, and allow the users to update the firmware by themselves.

13 Claims, 2 Drawing Sheets

DISPLAY FOR SHARING DISPLAY DATA CHANNEL

CROSS-REFERENCE TO RELATED APPLICATION

This application claims the priority benefit of Taiwan application serial no. 92127397, filed on Oct. 3, 2003, the full disclosure of which is incorporated herein by reference.

BACKGROUND OF THE INVENTION

1. Field of the Invention

This invention generally relates to a display for sharing display data channel (DDC), and more particularly to a display for sharing display data channel by using in system programming (ISP) to update the firmware of the microcontroller.

2. Description of Related Art

As the application of the embedded flash memory has become mature, more and more microcontrollers are embedded with flash memory and provide ISP function. That is, the content of the embedded flash memory can be updated via the interface without removing the flash memory from the circuit board. The prior art uses RS232 or $I^2C$ protocol as the interface for ISP. In addition, RS232 is an important interface for the production line in debugging and adjusting the products.

However, the display generally does not provide RS232 or $I^2C$ interfaces. Hence, when performing ISP or adjustment, a particular tool is required to connect the circuit board. After the ISP or adjustment is performed, this particular tool will be removed. The drawback of the prior art is that after the display is assembled, it is impossible to reconnect the particular tool to the circuit board for performing ISP or adjustment.

To improve the prior art, a 9-pin RS232 connector has been added on the display for performing ISP or adjustment on the production line. However, the additional device increases the cost and occupies the space of the display.

SUMMARY OF THE INVENTION

An object of the present invention is to provide a display for sharing the DDC. By sharing the DDC, the firmware of the display can be updated or adjusted without additional devices, thereby simplifying the manufacturing tools, enhancing the manufacturing efficiency, and allowing the users to update the firmware by themselves.

Another object of the present invention is to provide a display for sharing the DDC. It further uses the ability of the memory to support bi-directional communication in order to reduce some switches.

The present invention provides a display for sharing a display data channel, comprising: a microcontroller having a bi-directional interface and a switch-command output terminal; a memory having a serial data terminal and a serial clock terminal; a first switch having a data transmission connecting points set, a plurality of data selecting connecting points, and a switch-command receiving terminal, one of the plurality of data selecting connecting points being coupled to the two-wire interface, another one of the plurality of data selecting connecting points being coupled to the serial data terminal and the serial clock terminal, the switch-command receiving terminal being coupled to the switch-command output terminal, the data transmission connecting points set being coupled to a selected one of the plurality of data selecting connecting points based on a data received at the switch-command receiving terminal; and an interface connector having an interface, the interface being coupled to an external device and to the data transmission connecting points set.

The present invention provides a display for sharing a display data channel, comprising: a microcontroller having a two-wire interface, the two-wire interface having a first terminal and a second terminal; a memory, compliant with the display data channel protocol, having a serial data terminal and a serial clock terminal, the serial data terminal being coupled to the first terminal, the serial clock terminal being coupled to the second terminal; and an interface connector having an interface, the interface being coupled to an external device and to the first terminal/the serial data terminal and to the second terminal/the serial clock terminal; wherein the memory be switched into a bi-directional communication mode when the microcontroller uses the interface connector.

In a preferred embodiment of the present invention, the interface connector can be an analog RGB (D-sub) or digital visual interface (DVI) connector. The D-Sub connector further comprises a vertical synchronized signal terminal coupled to the VCLK terminal of the memory. The two-wire interface is compliant with $I^2C$ or RS232 interface protocols.

The display of the present invention shares the DDC and thus the preexisting DDC can be used as the interface for RS232 or $I^2C$ protocol for performing the ISP or adjustment of the firmware. Hence, the present invention can simplify the manufacturing tools, enhance the manufacturing efficiency, and allow the users to update the firmware by themselves.

The above is a brief description of some deficiencies in the prior art and advantages of the present invention. Other features, advantages and embodiments of the invention will be apparent to those skilled in the art from the following description, accompanying drawings and appended claims.

DESCRIPTION OF THE PREFERRED EMBODIMENTS

Most of the displays are embedded with microcontrollers. Most microcontrollers are embedded with the flash memory to provide ISP in order to update the firmware. That is, the content of the embedded flash memory can be updated via the interface without removing the flash memory from the circuit board. The prior art uses RS232 or $I^2C$ protocol as the interface for ISP. In addition, RS232 is an important interface for the production line in debugging and adjusting the products. The present invention provides a display using the preexisting DDC as the interface for RS232 or $I^2C$ protocol to perform the ISP or adjustment of the firmware.

Figure 1:
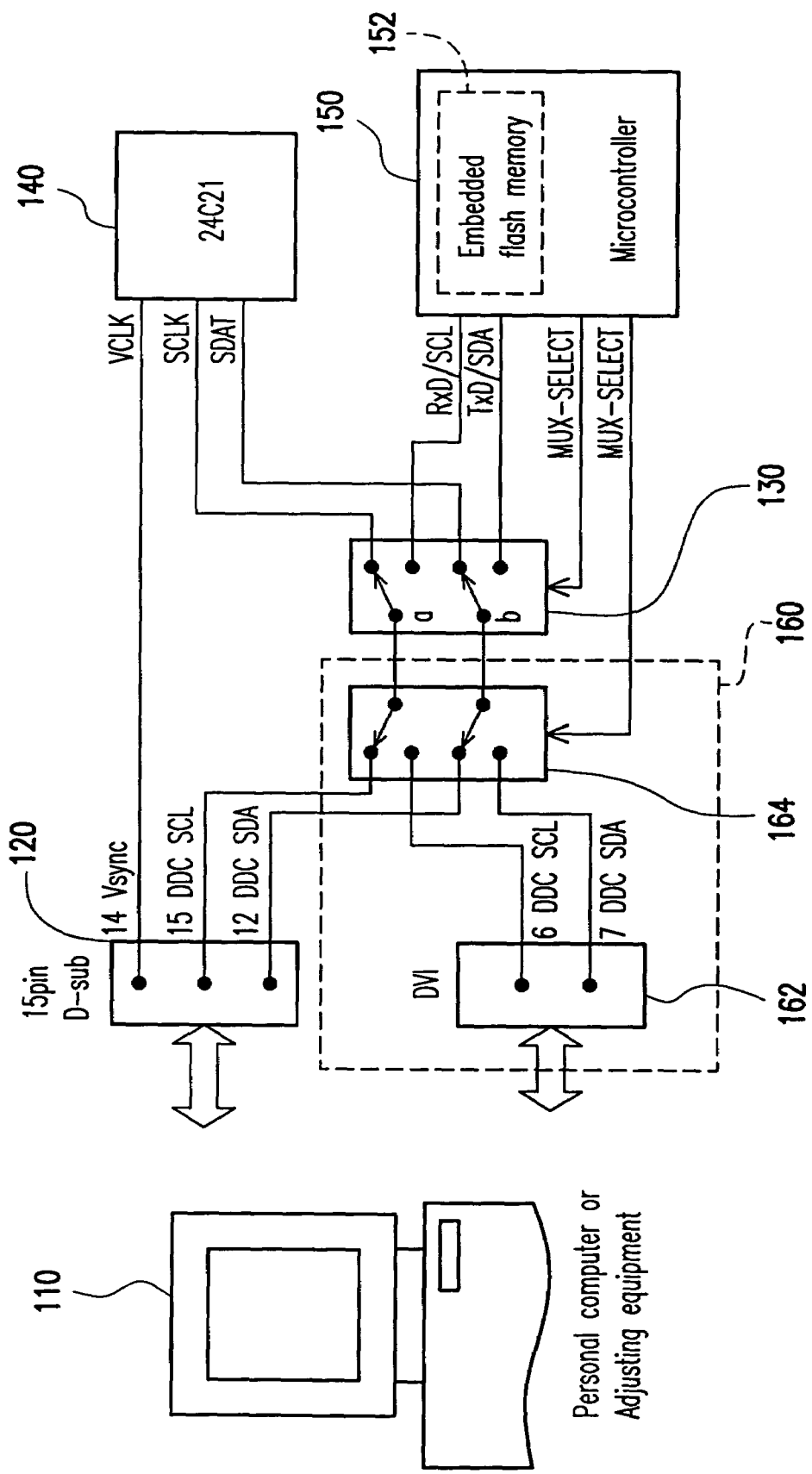
FIG. 1 is a block diagram in accordance with a preferred embodiment of the present invention.

FIG. 1 is a block diagram in accordance with a preferred embodiment of the present invention. Referring to FIG. 1, the computer 110 can be a personal computer, adjusting equipment on the production line, or other devices that can perform ISP. In this embodiment, the DDC of the analog video signal interface connector 120, such as the analog RGB (D-sub) connector, or the digital video signal interface connector 162, such as the digital visual interface (DVI)

connector, is used to function as the connector for RS232 or I²C protocol. The computer 110 sends the serial clock (SCL) and serial data (SDA) to the display via the 15th and 12th pins of the D-Sub connector 120 or via the 6th and 7th pins of the DVI connector 162. It depends on the connector the user selects so that the switch 164 can send the SCL and SDA to the switch 130. The switches 164 and 130 are double-pole-double-throw (DPDT) switches, which are controlled by the microcontroller 150 via the switch-command terminal. When the display operates under the normal circumstance, the switch 130 receives the SCL and SDA via data transmission points and switch-connects to one of the data selecting points in order to output them to the serial clock terminal (SCLK) and the serial data terminal (SDAT) of the memory 140, respectively.

In this embodiment, the memory 140 is a 24C21 chip. This memory is a 2-wire serial EEPROM in compliance with DDC1/DDC2 standard. Regarding the specification and function of the 24C21, please refer to the specification of the chip (model: AT24C21) provided by ATMEL. The pin VCLK of the memory is coupled to the 14th pin (Vsync) of the D-Sub connector 120 and to a pull-up circuit (not shown). The pull-up circuit keeps the pin VCLK of the memory 140 at high voltage level, when the 14th pin of the connector 120 is not connected to any device.

The microcontroller 150 has a 2-wire interface such as 8051 microcontroller. When the shared DDC is used for performing ISP, the switch 130 receives serial clock and serial data via data transmission points, and switch-connects to the data receiving terminal RxD/SCL and the data transmitting terminal TxD/SDA of the microcontroller 150, thereby storing the received data into the flash memory 152 or other memory the microcontroller 150 can use (not shown).

The second preferred embodiment is provided, which is similar to the above embodiment except that the connector module 160 is omitted. Referring to FIG. 1, the 15th pin of the connector 120 is coupled to the pin a of the data transmission points of the switch 130; the 12th pin of the connector 120 is coupled to the pin b of the data transmission points of the switch 130. The connector module 160 can be omitted because the display can only receive signal from a single source at any time; hence the idle interface connector can be omitted to reduce the cost. In this embodiment, the connector 162 is omitted; however, one skilled in the art can also choose to omit the connector 120 and the switch 164 so that the 6th pin of the connector 162 is coupled to the pin a of the data transmission points of the switch 130 and the 7th pin of the connector 162 is coupled to the pin b of the data transmission points of the switch 130.

Figure 2:
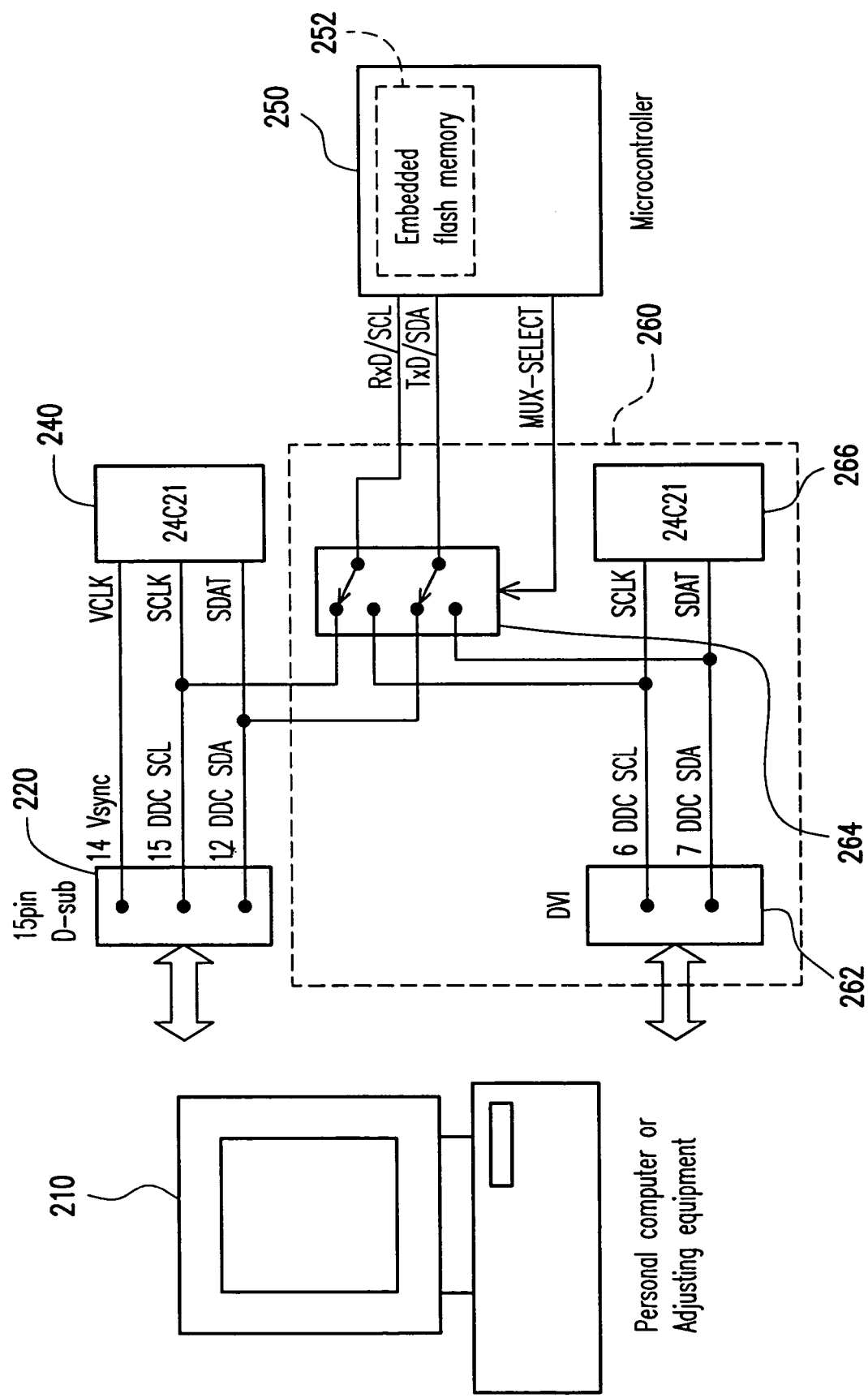
FIG. 2 is a block diagram in accordance with another preferred embodiment of the present invention.

If the data receiving terminal RxD and data transmitting terminal TxD of the microcontroller can also be used as GPIO pins, then the switch 130 can also be omitted. FIG. 2 is a block diagram in accordance with the third preferred embodiment of the present invention.

Referring to FIG. 2, the computer 210 can be a personal computer, adjusting equipment on the production line, or other devices that can perform ISP. In this embodiment, the DDC of the analog video signal interface connector 220, such as the analog RGB (D-sub) connector, or the digital video signal interface connector 262, such as the digital visual interface (DVI) connector, is used to function as the connector for RS232 or I²C protocol. The computer 210 sends the serial clock (SCL) and serial data (SDA) to the display via the 15th and 12th pins of the D-Sub connector 220 or via the 6th and 7th pins of the DVI connector 262. It depends on the connector the user selects so that the switch 264 can send the SCL and SDA to the microcontroller 250. The switch 264 is double-pole-double-throw (DPDT) switch, which is controlled by the microcontroller 250 via the switch-command terminal. To illustrate the present invention, we only use the D-sub connector 220 as an example. One skilled in the art would know that the switch 264 can be connected to the DVI connector 262 or other connectors that can provide DDC for 2-wire data transmission, and the same result can be achieved.

The microcontroller 250 provides a 2-wire interface such as 8051 microcontroller. The memories 240 and 266 have to support the DDC standard. Taking 24C21 chip as an example, this memory by default supports the transmit-only mode of the DDC1 standard. The pin VCLK of the memory 240 is coupled to the 14th pin (Vsync) of the D-Sub connector 220 and to a pull-up circuit (not shown). The pull-up circuit keeps the pin VCLK of the memory 240 at high voltage level, when the 14th pin of the connector 220 is not connected to any device. The pin VCLK of the memory 266 is also coupled to a pull-up circuit (not shown).

When the display operates under the normal circumstance, the memory 240 receives the serial clock and serial data from the computer 210 via the connector 220; the memory 266 receives the serial clock and serial data from the computer 210 via the connector 262. When the shared DDC is used for performing ISP, the switch 264 receives serial clock and serial data from the connector 220 via one data selecting point, and switch-connects to the data receiving terminal RxD/SCL and the data transmitting terminal TxD/SDA of the microcontroller 250, thereby storing the received data into the flash memory 252 or other memory the microcontroller 250 can use (not shown). Because the memory 240 will continues to send out a sequence of data via the SDAT under the transmit-only mode, if the ISP is performed under the transmit-only mode, the data transmitting terminal TxD/SDA of the microcontroller 250 will be interfered by the data sent out from the memory 240. Hence, the operation mode of the memory 240 has to be switched into the bi-directional mode to support the DDC2 standard. Further, if the DVI connector is used, because DVI connector cannot provide vertical synchronized signal Vsync, the chip 24C21 has to be switched into the bi-directional mode either. Regarding the DDC1 and DDC2 standards, please refer to the Enhanced Display Data Channel Standard (E-DDC Standard) provided by VESA.

Under the bi-directional mode, the input signals to the pin VCLK of the memory 240 will be ignored. Because the I²C protocol has a rigid condition for start, stop, and addressing, the memory 240 under bi-directional mode will not interfere with the ISP. The memory 240 can be switched from the transmit-only mode to the bi-directional mode by issuing a high to low transition on the SCLK pin. Regarding the operation mode switch of the chip 24C21, please refer to the specification of the chip (model: AT24C21) provided by ATMEL.

The data receiving terminal RxD and data transmitting terminal TxD of the microcontroller such as 8051 can also be used as GPIO pins. Hence, the operation mode switch signal required by 24C21 can be easily generated via the data receiving terminal RxD of the microcontroller. Further, the data receiving terminal RxD and data transmitting terminal TxD of some enhanced microcontrollers based on 8051 (such as Myson's MTV312M64 and MTV412M) can function as a hardware I²C interface. The enhanced microcontroller provides a hardware I²C address for PC or external equipment addressing and ISP.

The fourth preferred embodiment is provided, which is similar to the third embodiment except that the connector module 260 is omitted. Referring to FIG. 2, the 15$^{th}$ and 12$^{th}$ pins of the connector 220 are coupled to the data receiving terminal RxD/SCL and data transmitting terminal TxD/SDA of the microcontroller 250, respectively. The connector module 260 can be omitted because the display can only receive signal from a single source at any time; hence the idle interface connector can be omitted to reduce the costs. In this embodiment, the connector 262 is omitted; however, one skilled in the art can also choose to omit the connector 220, the memory 240, and the switch 264 so that the 6$^{th}$ pin of the connector 262 and the SCLK of the memory 266 are coupled to the data receiving terminal RxD/SCL of the microcontroller 250 and the 7$^{th}$ pin of the connector 262 and the SDAT of the memory 266 are coupled to the data transmitting terminal TxD/SDA of the microcontroller 250.

The above description provides a full and complete description of the preferred embodiments of the present invention. Various modifications, alternate construction, and equivalent may be made by those skilled in the art without changing the scope or spirit of the invention. Accordingly, the above description and illustrations should not be construed as limiting the scope of the invention which is defined by the following claims.

What is claimed is:

1. A display for sharing a display data channel, comprising:
   a microcontroller with a non-volatile memory for storing a firmware, having a two-wire interface and a switch-command output terminal;
   a memory for supporting display data channel standard, having a serial data terminal and a serial clock terminal;
   a first switch, having a data transmission connecting points set, a plurality of data selecting connecting points, and a switch-command receiving terminal, one of said plurality of data selecting connecting points being coupled to said two-wire interface, another one of said plurality of data selecting connecting points being coupled to said serial data terminal and said serial clock terminal, said switch-command receiving terminal being coupled to said switch-command output terminal, said data transmission connecting points set being coupled to a selected one of said plurality of data selecting connecting points based on a data received at said switch-command receiving terminal; and
   an interface connector, having an interface, said interface being coupled to an external device and to said data transmission connecting points set, thereby allowing the firmware stored in the non-volatile memory to be updated by the external device.

2. The display of claim 1, wherein said interface connector is an analog RGB (D-sub) connector.

3. The display of claim 1, wherein said interface connector is a digital visual interface (DVI) connector.

4. The display of claim 1, wherein said interface connector further comprises a vertical synchronized signal terminal coupled to a clock signal receiving (VCLK) terminal of said memory.

5. The display of claim 1, further comprising:
   a second switch coupled to a plurality of interface connectors and to said data transmission connecting points set, said second switch selectively connecting one of said plurality of interface connectors to said data transmission connecting points set.

6. The display of claim 1, wherein said two-wire interface is compliant with the I$^2$C interface protocol.

7. The display of claim 1, wherein said two-wire interface is compliant with the RS232 standard.

8. A display for sharing a display data channel, comprising:
   a microcontroller with a non-volatile memory for storing a firmware, having a two-wire interface, said two-wire interface having a first terminal and a second terminal;
   a memory for supporting display data channel standard, compliant with the display data channel protocol, having a serial data terminal and a serial clock terminal, said serial data terminal being coupled to said first terminal, said serial clock terminal being coupled to said second terminal; and
   an interface connector, having an interface, said interface being coupled to an external device and to said first terminal/said serial data terminal and to said second terminal/said serial clock terminal;
   wherein said memory is switched into a bi-directional communication mode when said microcontroller uses said interface connector, thereby allowing the firmware stored in the non-volatile memory to be updated by the external device.

9. The display of claim 8, wherein said two-wire interface is compliant with the I$^2$C interface protocol.

10. The display of claim 8, wherein said two-wire interface is compliant with the RS232 standard.

11. The display of claim 8, wherein said interface connector is an analog RGB (D)-sub) connector.

12. The display of claim 8, wherein said interface connector is a digital visual interface (DVI) connector.

13. The display of claim 8, further comprising:
   a switch, coupled to a plurality of interface connectors, said microcontroller, and said memory, said switch selectively connecting one of said plurality of interface connectors to said microcontroller and said memory.

* * * * *